United States Patent [19]
Wynkoop

[11] Patent Number: 5,336,053
[45] Date of Patent: Aug. 9, 1994

[54] METHOD OF TESTING FOR LEAKAGE IN A SOLUTION PUMPING SYSTEM

[75] Inventor: Richard D. Wynkoop, Des Plaines, Ill.

[73] Assignee: Abbott Laboratories, Abbott Park, Ill.

[21] Appl. No.: 10,728

[22] Filed: Jan. 29, 1993

[51] Int. Cl.$^5$ .............................................. F04B 51/00
[52] U.S. Cl. ......................................... 417/53; 73/40
[58] Field of Search ........................ 417/9, 53, 413 R; 73/40, 168

[56] References Cited

U.S. PATENT DOCUMENTS

| | | | |
|---|---|---|---|
| 2,889,782 | 6/1959 | Smith | 417/413 R |
| 4,086,036 | 4/1978 | Hagen et al. | 417/413 R |
| 4,840,542 | 6/1989 | Abbott | 417/9 |
| 5,174,722 | 12/1992 | Lybecker | 417/9 |

Primary Examiner—Richard A. Bertsch
Assistant Examiner—Timothy S. Thorpe
Attorney, Agent, or Firm—A. Nicholas Trausch

[57] ABSTRACT

A method of testing a pumping system including a pump cassette effects pressurization of the system, with subsequent monitoring of any pressure loss in the system. This is achieved by closing any inlets and outlets of the cassette, and thereafter over-pressurizing the cassette beyond its normal operating range. Pressure measurements are taken before and after a specified time interval, with any significant pressure loss indicating system leakage. In the preferred practice, the diaphragm of the pump cassette is first subjected to cold flow, or "creep", thereby minimizing the influence of cold flow of the diaphragm on subsequent pressure measurement.

10 Claims, 5 Drawing Sheets

METHOD OF TESTING FOR LEAKAGE IN A SOLUTION PUMPING SYSTEM

TECHNICAL FIELD

The present invention generally relates to a solution pumping system which can be advantageously employed for preparation of patient parenteral solutions, and more particularly a method of testing a pump cassette of the system for liquid leakage.

BACKGROUND OF THE INVENTION

Healthcare facilities require preparation and administration of very large numbers of parenteral solutions for patients. Such solutions are administered for both nutritional and therapeutic purposes, and thus efficient liquid-handling systems are required for cost-effective preparation of such solutions, and their administration to patients.

To this end, positive displacement fluid pumping devices have been developed for both preparation and administration of parenteral solutions. Such devices permit precise control during pumping of solutions, thus facilitating solution administration and preparation.

U.S. Pat. Nos. 4,639,245, to Pastrone et al., 4,818,186, to Pastrone et al., and 4,842,584, to Pastrone, all of which are hereby incorporated by reference, disclose a positive displacement fluid infusion pumping device and components thereof, which have met with widespread acceptance by the healthcare industry. This pumping system includes a combination of a pump driver and an associated removable and disposable pump cassette. The pump cassette includes a self-contained positive displacement pump device, which is operated by a reciprocable pump plunger or piston of the associated pump driver. The pump driver includes selectively operable valve actuators, which cooperate with valve mechanisms provided in the pump cassette for accurate and highly automated administration and infusion of parenteral solutions.

Commonly-assigned U.S. patent application Ser. No. 07/444,459, filed Dec. 1, 1989, now U.S. Pat. No. 5,062,774 issue Nov. 5, 1991, discloses a solution pumping system generally of the above type, including a disposable pump cassette, and an associated pump driver. The system of this application is particularly configured for automatic compounding and preparation of parenteral solutions, for subsequent infusion to a patient. This application is hereby incorporated by reference.

Solution pumping systems of the above type employ pre-assembled, disposable pump cassettes. Typically, such pump cassettes include a cassette body having juxtaposed front and rear body members, between which is positioned a membrane-like elastomeric diaphragm. The diaphragm cooperates with the front body member to provide valve mechanisms at various inlets and outlets defined by the front body member, with openings in the rear body member exposing the diaphragm for operation of the valve mechanisms by valve actuators of the associated pump driver.

Additionally, the front body member of the cassette defines a pump chamber, which, together with the internal diaphragm, provides the self-contained positive displacement pump of the cassette. The rear body member defines an opening through which a reciprocable pump piston of the associated driver is movable for operating the cassette, whereby liquid can be pumped through the cassette.

As will be appreciated, use of the above-described pumping system for preparation of parenteral solutions, or for infusion of such solutions, mandates that the system perform reliably and with a high degree of accuracy. Accordingly, such systems are ordinarily constructed to exhibit a high degree of structural integrity, with the pump cassette of such system typically constructed in a manner to all but eliminate the possibility of liquid leakage. Nevertheless, normal manufacturing variances may result in a cassette lacking the desired sealing integrity. Additionally, use of the cassette in association with the pump driver of the system may result in wear and impairment of its sealing.

Because leakage, even of a minor nature, in the pump cassette could inadvertently result in improper solution preparation, the present method contemplates a method of operating the pumping system for periodically testing the sealing integrity of the pump cassette.

SUMMARY OF THE INVENTION

The present invention is directed to a method of operating a solution pumping system, which in the illustrated embodiment includes a pump cassette and an associated pump driver, in a manner which permits periodic testing of the sealing integrity of the pump cassette to detect any liquid leakage in the device. This is achieved by operating the pump of the cassette to pressurize liquid therein, and monitoring the liquid pressure to ascertain any significant pressure drop. In the preferred practice of the invention, prior to testing, the elastomeric diaphragm of the pump cassette is displaced, with the valves of the cassette closed, so that the liquid pressure created in the cassette is beyond the normal range. The diaphragm is then partially retracted after a brief time interval. Testing for a pressure drop is then performed, with this somewhat prolonged stretching, and subsequent relaxation, of the diaphragm substantially eliminating any significant liquid pressure drop resulting from cold flow of the elastomeric diaphragm during testing. Accurate testing for leakage is thus facilitated.

One aspect of the present invention contemplates a method of testing a pumping system which includes a pump which creates a positive liquid pressure in the system during a pumping stroke. The present method is particularly adapted for testing the integrity of a pump cassette of the system, wherein the system includes a pump driver having a reciprocable pump piston, with the pump of the cassette including a diaphragm positionable in operative association with the pump piston.

As noted, testing for leakage is achieved by operating the pump of the system to create a positive liquid pressure therein. More specifically, testing of the system pump cassette is achieved by operating the pump driver to close the liquid inlets and outlets of the pump cassette. A positive liquid pressure is created therein by advancing the pump piston of the driver to displace the diaphragm to a first position.

To assure the accuracy of the test method, displacement of the diaphragm to the first position creates a relatively high pressure in the system, thereby stretching the diaphragm. The diaphragm is thereafter maintained in the first position for a predetermined time interval, thereby intentionally inducing cold flow of the diaphragm. The pump piston is subsequently retracted so that the diaphragm moves to a second position wherein it is displaced less than in the first position. This preferred practice of the present method desirably acts to minimize the effect of cold flow, or "creep", of the diaphragm during testing for pressure loss in the system. As a result, any detected pressure loss in the system can be attributed to system leakage, and is not significantly affected by cold flow of the diaphragm.

Thus, displacement of the diaphragm to the first position, with all of the inlets and outlets closed, effectively results in the system being over-pressurized, that is, pressurized beyond its usual operating range. This pressure is maintained sufficiently high for a sufficient time interval to subject the stretched diaphragm to cold flow. During subsequent operation, particularly during leakage testing, the influence of any cold flow is substantially eliminated.

After the diaphragm has been moved to its second position by retraction of the pump piston, the pressure of liquid in the cassette of the system is measured to obtain a first pressure $P_1$. Testing continues by waiting a predetermined time interval after measurement of $P_1$ (approximately 15 seconds, as will hereinafter be explained in detail), with the pressure of liquid in the cassette of the system again measured to obtain a second liquid pressure $P_2$.

The accuracy of each of the measurements of the pressure in the system is facilitated by obtaining an average pressure in the system over a predetermined time interval at each measurement.

The pressure $P_1$ and the pressure $P_2$ are next compared to ascertain any drop of pressure in the cassette of the system. In the event that the pressure drop exceeds a predetermined value, a signal is provided indicating leakage in the cassette of the system, with a suitable alarm or the like provided for operating personnel to alert them to the condition.

By performing the present test at the conclusion of preparation of each bag or like container of parenteral solution, proper operation of the system during preparation of that bag is easily and reliably checked. The testing method is then again preferably repeated at the conclusion of preparation of the next bag of solution.

Other features and advantages of the present invention will become readily apparent from the following detailed description, the accompanying drawings, and the appended claims.

DETAILED DESCRIPTION

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

For purposes of disclosing the present invention, operation of an exemplary solution pumping system will be discussed in detail. As will be appreciated, the controls of the system are preferably programmable to perform the sequence of steps of the present invention in an automated fashion. Efficient, predictable, and reliable operation of the pumping system is achieved in this manner, with the present method providing efficient periodic testing of the system.

Figure 1:
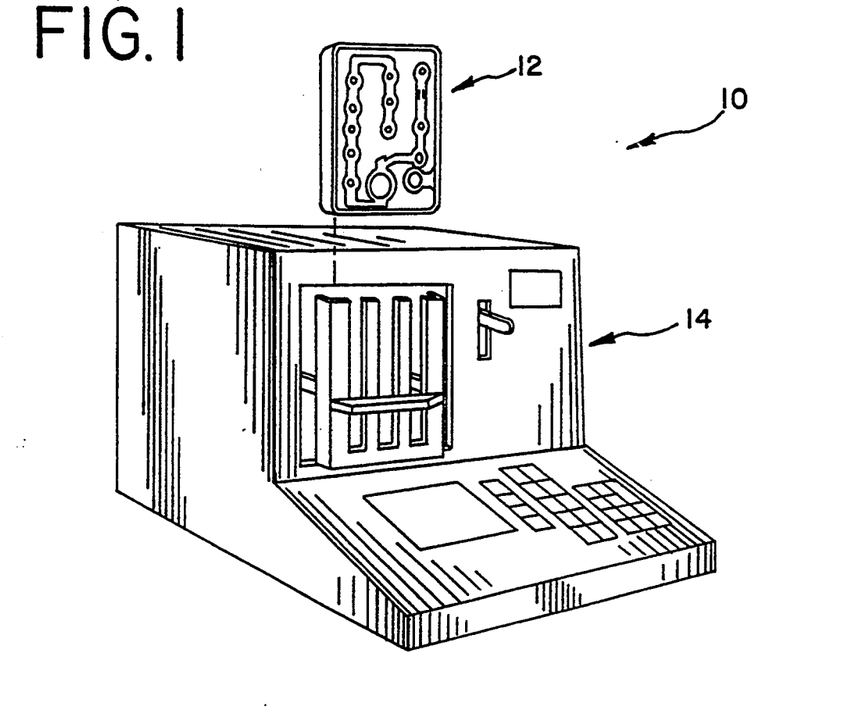
FIG. 1 is a perspective view of a solution pumping system, including a pump driver and a disposable pump cassette, which is operable in accordance with the principles of the present invention.

With reference now to the drawings, therein is illustrated a solution pumping system 10 operable in accordance with the principles of the present invention. The illustrated system is shown in the form of a so-called solution compounder, that is, a system particularly suited for compounding and preparation of parenteral solutions for subsequent administration to patients. However, it will be appreciated that a system operable in accordance with the principles disclosed herein can be readily configured for infusion of such solutions, or for other applications.

The solution pumping system includes a disposable pump cassette 12 which is removably positionable in operative association with a pump driver 14. For use in compounding parenteral solutions, the system is joined, via appropriate tubing sets, with containers of solutions to be compounded, and with a container into which appropriate quantities of the various solutions are mixed. The resultant admixture is thus ready for patient administration. Because this type of system is capable of efficiently and accurately preparing very large numbers of such admixtures, the system would ordinarily be used in the pharmacy of a healthcare facility, preferably within a laminar-flow hood.

U.S. patent application Ser. No. 07/444,459, filed Dec. 1, 1989, now U.S. Pat. No. 5,062,774, issued, Nov. 5, 1991 hereby incorporated by reference, discloses in greater detail features of the illustrated solution pumping system. The disposable pump cassette 12 of the system, as particularly illustrated in FIGS. 2 and 3, includes a cassette body comprising juxtaposed front and rear body members 18 and 20, and a membrane-like elastomeric diaphragm 22 positioned in sandwich-like relationship between the front and rear cassette members.

Figure 2:
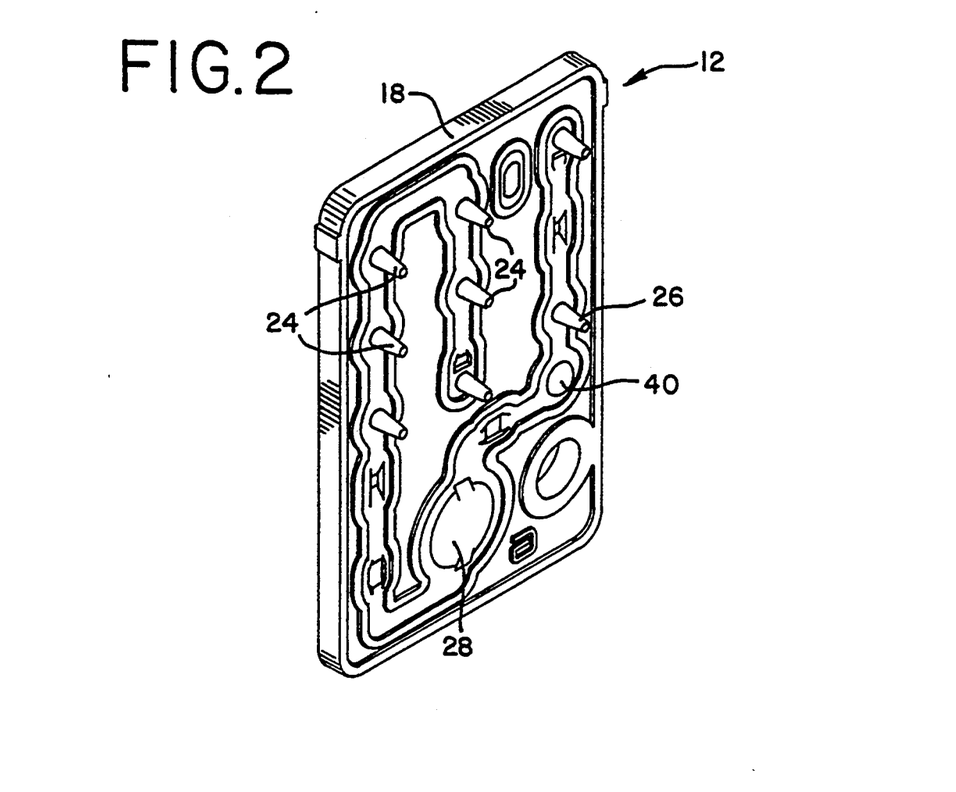
FIG. 2 is a perspective view of the pump cassette illustrated in FIG. 1.
Figure 3:
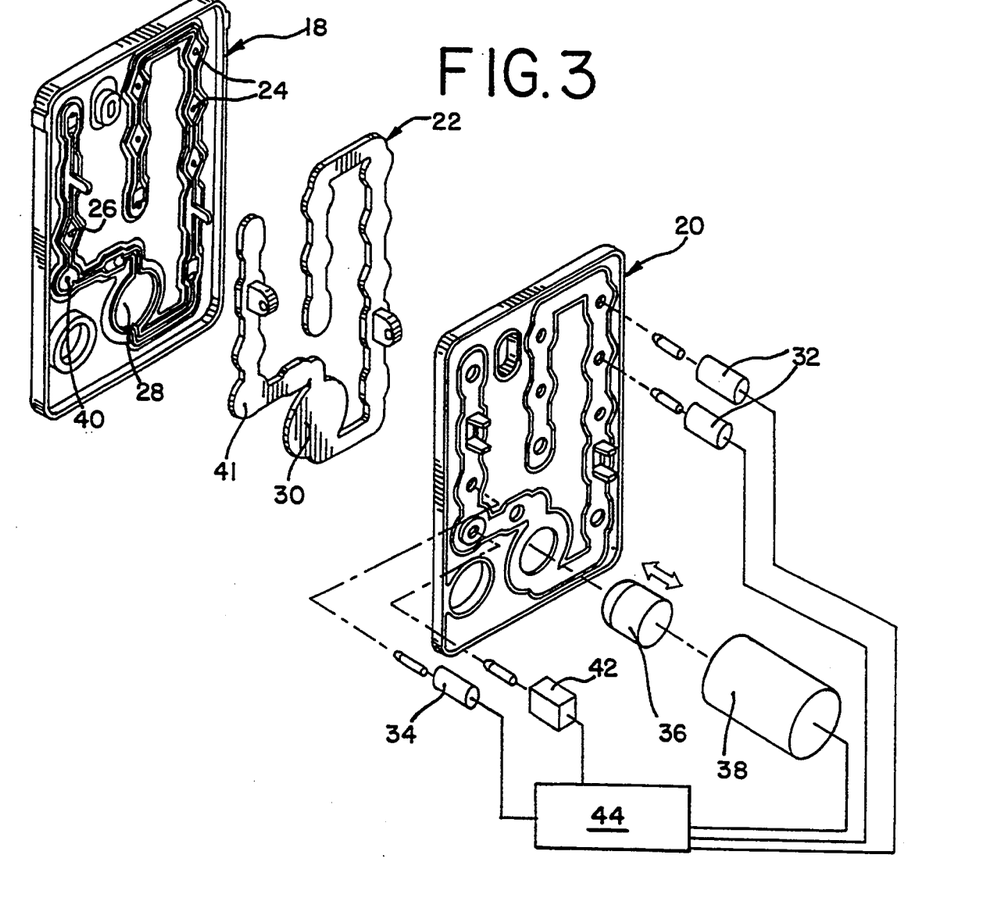
FIG. 3 is a diagrammatic, exploded perspective view illustrating the construction of the pump cassette shown in FIG. 2, and the manner in which components of the associated pump driver cooperate with the pump cassette.

The front and rear cassette members are joined to each other, such as by ultrasonic welding, such that the rear cassette member holds the elastomeric diaphragm 22 in tightly conforming relationship with the front cassette member 18. In this way, the diaphragm and the front cassette member together define a liquid flow path through which liquid flows within the cassette.

The cassette includes at least one, and preferably a plurality, of liquid inlets 24 which are configured to be joined via suitable tubing to containers of the various solutions to be compounded. The cassette further includes at least one liquid outlet 26 which is connected by suitable tubing to the container which receives the solution admixture being prepared.

Figure 4:
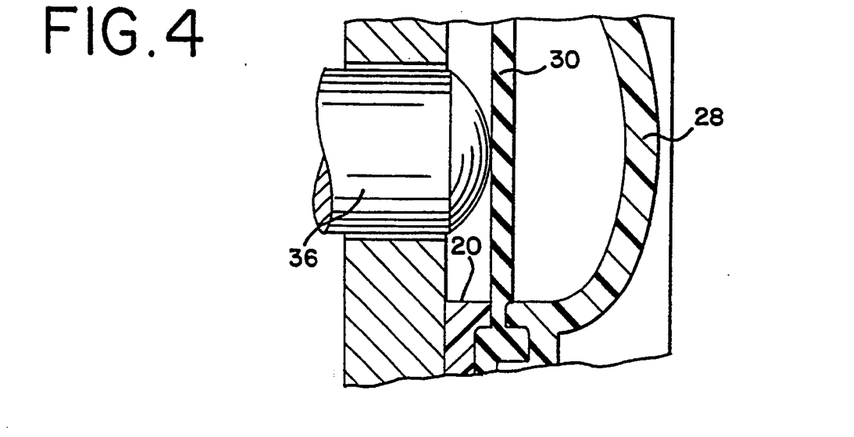
FIG. 4 is a fragmentary cross-sectional view illustrating a pump chamber of the pump cassette of the present system.

Pumping of liquid through the cassette is effected by a self-contained positive displacement pump of the assembly. In particular, the front cassette member 18 includes a bowl-like pump chamber 28, with the diaphragm 22 including a pump portion 30 positioned adjacent to the pump chamber 28.

Control of liquid flow through the cassette is effected by a plurality of solenoid-operated valve actuators of the pump driver 14. The valve actuators are operable through openings defined by the rear cassette member 20, with the actuators acting against respective portions of the diaphragm 22 to cooperate in a valve-like manner with valve seats defined by the front cassette member 18. Thus, each of the various liquid inlets 24 is controlled by a respective valve actuator 32, with the liquid outlet 26 similarly controlled by a respective valve actuator 34.

Operation of the positive displacement pump of the cassette is effected by a reciprocable pump piston or plunger 36 of the pump driver 14. Operation of the pump is in accordance with above-referenced U.S. Pat. No. 4,639,245, to Pastrone et al. Essentially, liquid flow is effected by reciprocation of the pump piston 36 in timed relation to operation of inlet and outlet actuators 32 and 34. A reversible stepping motor 38, acting through a suitable threaded connection, provides reciprocable stroking of the pump piston for alternately deforming and relaxing the pump portion 30 of the diaphragm 22, thus affecting positive displacement of liquid in the pump chamber 28. During the advancing stroke of the pump piston 36, the diaphragm portion 30 is displaced into the pump chamber, with outlet 26 being opened by appropriate operation of its actuator 34. Liquid displacement on the order of 0.76 ml is typical in a current embodiment. During the return stroke of the pump piston, the outlet is closed, and an appropriate one of the inlets 24 is opened by operation of its respective actuator 32. During the return stroke, the resilient pump portion 30 of the diaphragm creates a negative pressure within the pump chamber, thus refilling the chamber with liquid for completing the pump cycle.

In order to monitor liquid pressures created within the pump cassette by the positive displacement pump, the present system preferably includes a pressure sensor 34 incorporated into pump driver 14. Front cassette member 18 defines a pressure chamber 40, with the diaphragm 22 including a portion 41 adjacent the pressure chamber, which portion 41 is engaged by a probe-like portion of the pressure sensor 42. The pressure sensor 42 is operatively connected with automated, programmable controls 44 of the present system. The controls 44 are preferably integrated into the pump driver 14, with the controls operatively connected with the various valve actuators, stepper motor 38, and other sensors of the system for effecting integrated operation thereof, including testing the pump cassette of the system for any leakage, as contemplated by the present invention.

Operation of the illustrated system is preferably effected in a manner which acts to minimize peak pumping pressures within the cassette 12, while maximizing liquid output of the device. In essence, this is achieved by operating the pump piston 36, and thus the positive displacement pump of the cassette, in a manner which creates a "square" pressure waveform. While the waveform is not truly "square", a practical impossibility, it is contemplated that during each pumping cycle, the system pressure is rapidly increased to the desired maximum, held at that desired limit until liquid from pump chamber 28 is displaced, and thereafter effecting refilling of the pump chamber as quickly as possible for the subsequent pump cycle. This is achieved by selectively varying the velocity of the pump piston during each advancing stroke, and preferably also during the return stroke.

Figure 5:
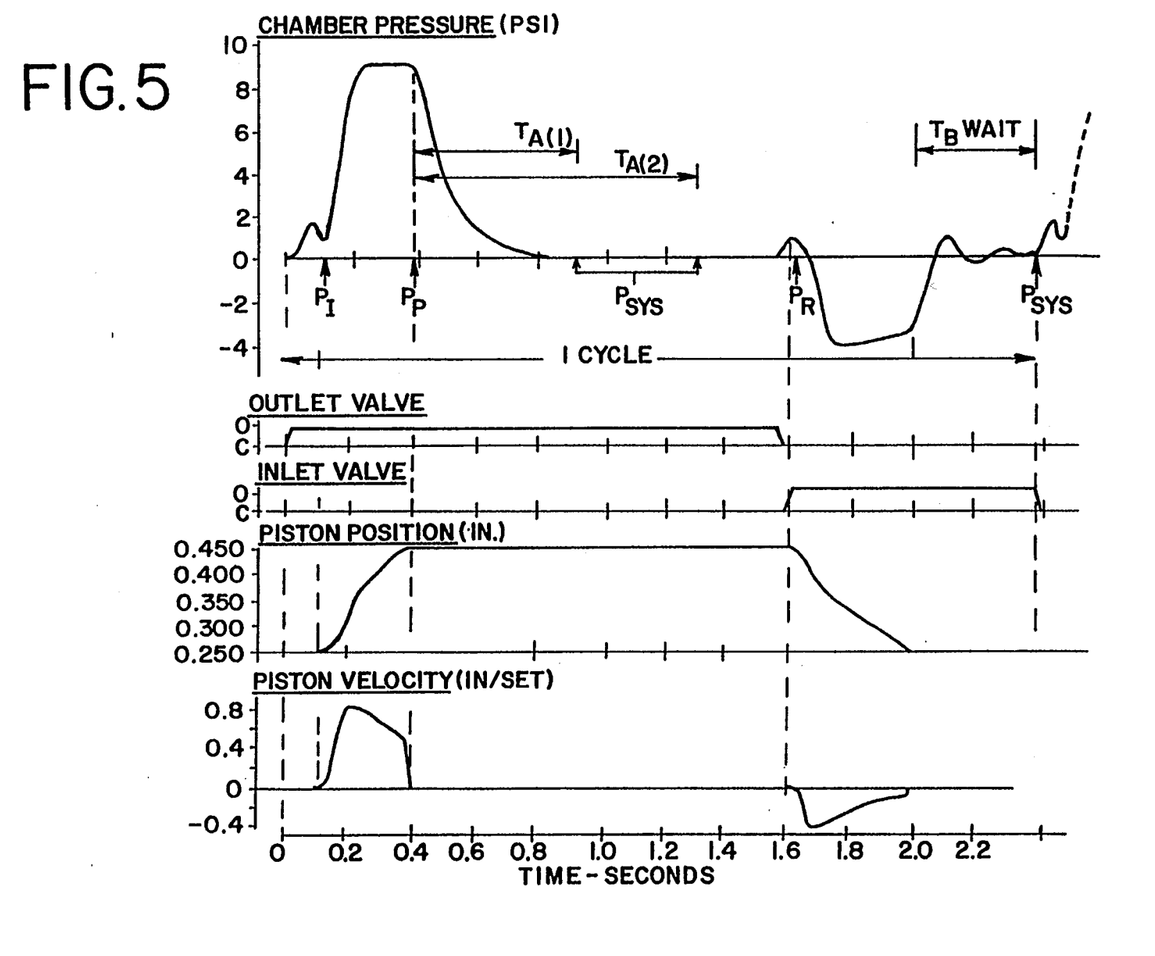
FIG. 5 illustrates a series of timing diagrams illustrating the operation of the pumping system in accordance with the present method during a pump cycle.

FIG. 5 illustrates timing diagrams associated with a single pump cycle, i.e., one advancing stroke and return stroke of the pump piston 36 acting in cooperation with the pump portion 30 of the diaphragm 32.

Figure 6:
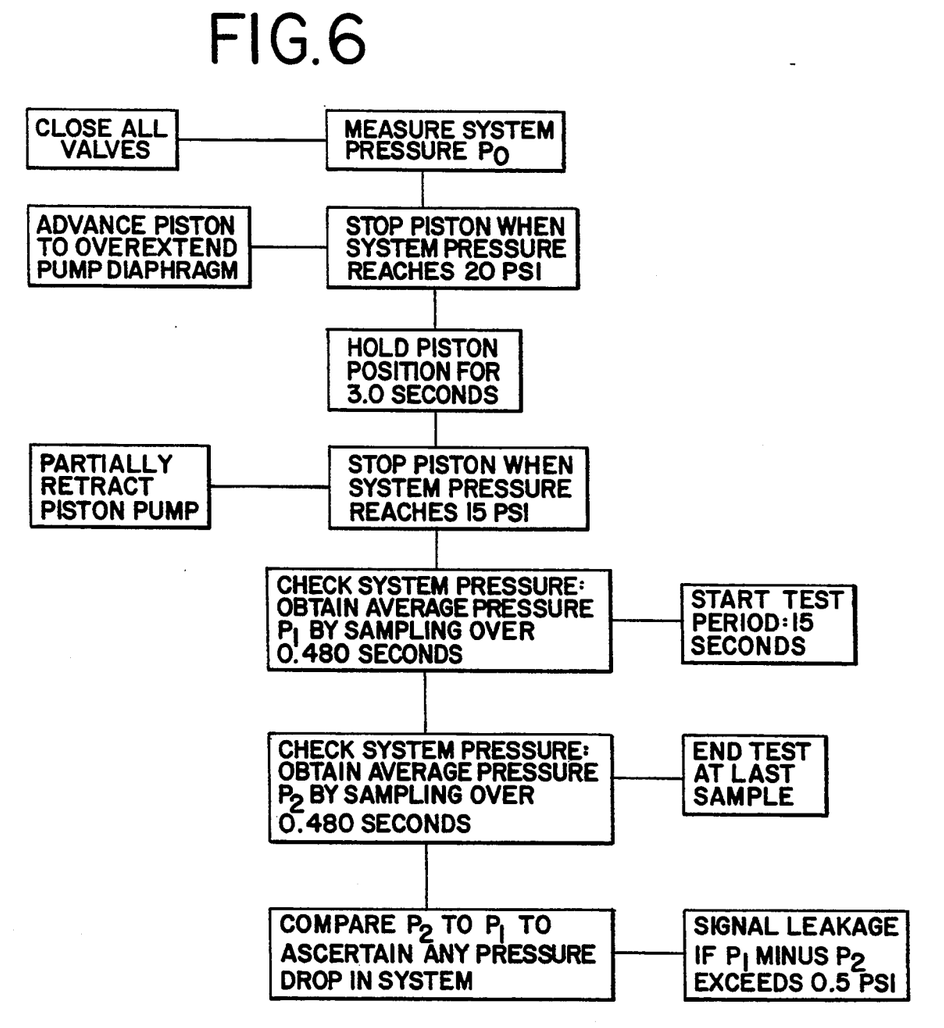
FIG. 6 is a flow diagram illustrating the sequence of steps of the present method.
Figure 7:
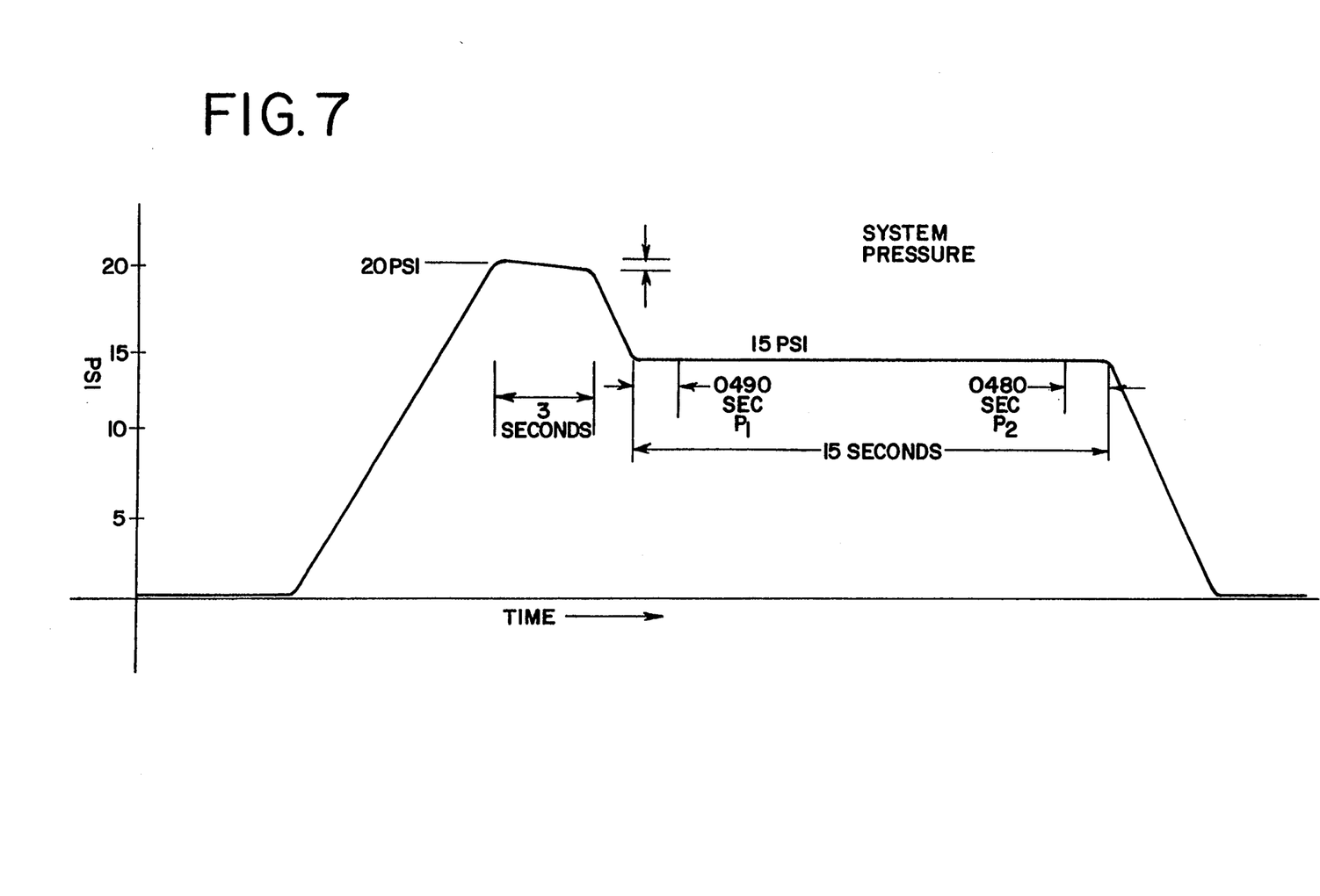
FIG. 7 is a diagram generally illustrating pressure within the solution pumping system during testing in accordance with the method of the present invention.

With reference now to FIGS. 6 and 7, the method of operating the present system for testing for leakage will now be described. The sequence of steps of the testing method are set forth in the flow diagram of FIG. 6, with the diagram of FIG. 7 (not to scale), graphically illustrating pressure within the system during testing.

In practicing the preferred form of the present method, which is particularly suited for testing the sealing integrity of pump cassette 12 of the system, the pump driver 14 is first operated to close all of the inlets and outlets of the pump cassette by appropriate operation of valve actuators 32, 34. This is preferably performed after the system has been used for preparation of a bag or other container of parenteral solution (or after another pumping operation in a different application), so that the pump cassette is filled with liquid for purposes of testing. At this time, controls 44 monitor the system pressure $P_0$ via pressure sensor 42.

Prior to the taking of pressure readings in the system for ascertaining any pressure loss, it is particularly preferred that the system be operated to eliminate, to the extent possible, the influence of cold flow, or "creep", of the pump portion 30 of the diaphragm on the leakage test. This is achieved by advancing the pump piston 36 to displace and stretch the pump diaphragm, with the inlet and outlet valves of the cassette closed, to create a relatively high liquid pressure in the cassette of the system. In a current embodiment, this initial diaphragm displacement corresponds to pressurizing the system to 20 psi, a relatively high liquid pressure in the cassette of the system.

The stretched diaphragm is maintained in this first position for a predetermined time interval (3.0 seconds in a current embodiment). This relatively prolonged pressurization of the system acts to intentionally induce cold flow of the diaphragm, which has been found to very substantially reduce the effect of cold flow on subsequent measurement for pressure drop. As illustrated in FIG. 7, the diaphragm may undergo some cold flow while it is maintained in this stretched condition, resulting in a slight pressure drop, designated "c" in FIG. 7.

The pump piston 36 is next operated, via stepper motor 38, to move the pump diaphragm to a second position, wherein the diaphragm is displaced less than in the first position. This is illustrated in FIG. 7, wherein system pressure is reduced, in a current embodiment to 15 psi. Not only does this preferred sequence of steps substantially obviate the influence of cold flow on subsequent pressure measurement, testing is preferably performed at pressures substantially beyond those at which the system normally operates, again acting to identify any potential leakage before it is likely to occur during normal pumping operations.

Pressure measurements are now taken for purposes of ascertaining any pressure loss in the cassette of the system while the pressure is maintained at this elevated system pressure. In the preferred practice of the present method, accuracy in pressure measurement is assured by obtaining an average pressure in the cassette of the system over a predetermined time interval. In current practice, 60 sample readings are taken over 0.480 seconds, with averaging of these readings providing the measured pressure $P_1$.

Subsequent to measurement of $P_1$, the present method contemplates waiting a predetermined time interval before the next measurement of system pressure. Waiting of this time interval facilitates detection of any significant pressure drop, even if relatively small in value, as the system is maintained at a pressure beyond the normal range. In a current embodiment, the time interval after measuring pressure $P_1$ is approximately 15 seconds. Specifically, the controls operate to provide a 15 second interval which is timed from the beginning of the sampling for pressure reading $P_1$, and which concludes at the conclusion of sampling for pressure $P_2$.

In taking pressure $P_2$, it is also contemplated that 60 samples be taken over a 0.480 second predetermined time interval.

The controls 44 of the system next compare $P_2$ to $P_1$ to ascertain any pressure drop in the system. In a current embodiment, a signal is provided indicating leakage in the cassette of the system when the difference between $P_1$ and $P_2$ exceeds 0.5 psi. In the event that leakage is detected, the cassette of the system is easily replaced, and any admixtures of parenteral solutions prepared since the previous leakage test are disposed of. Thus, periodic testing of the system assures the quality of parenteral admixtures being prepared.

From the foregoing, it will be observed that numerous modifications and variations can be effected without departing from the true spirit and scope of the novel concept of the present invention. It is to be understood that no limitation with respect to the specific embodiment is intended or should be inferred. The disclosure is intended to cover, by the appended claims, all such modifications as fall within the scope of the claims.

What is claimed is:

1. A method of testing a pumping system including pump means which creates a positive liquid pressure in the system during a pumping stroke, said method comprising the steps of:

operating said pump means to create a positive liquid pressure within the pumping system;

measuring the pressure of liquid in the system to obtain a first liquid pressure $P_1$;

waiting a predetermined time interval after measurement of pressure $P_1$;

measuring the pressure of liquid in the system to obtain a second liquid pressure $P_2$;

comparing the pressure $P_1$ to the pressure $P_2$ to ascertain any drop in pressure in the system; and providing a signal indicating leakage in the system when the difference between $P_1$ and $P_2$ exceeds a predetermined value.

2. The method of testing a pumping system in accordance with claim 1, wherein each of said steps of measuring the pressure of liquid in the system includes obtaining an average pressure of said system over a predetermined time interval.

3. The method of testing a pumping system in accordance with claim 1, wherein said step of operating said pump means includes first operating said pump means to create a relatively high liquid pressure in the system, and thereafter operating said pump means to reduce the pressure in the system prior to measuring the pressure to obtain pressure $P_1$.

4. A method of operating a pumping system, including positive displacement pump means having a deformable pump diaphragm which is displaced for creating positive liquid pressure in the system, the method comprising the steps of:

displacing said pump diaphragm to a first position to create a relatively high pressure in the system to stretch the pump diaphragm;

maintaining said pump diaphragm in said first position for a predetermined time interval; and thereafter operating said pump means at a system pressure less than said relatively high pressure, with said displacing and maintaining steps acting to reduce the influence of any of cold flow of said diaphragm.

5. A method of operating a pumping system in accordance with claim 4, including moving said diaphragm to a second position, monitoring the liquid pressure in said system to detect any leakage in the system.

6. A method of operating a pumping system in accordance with claim 5, wherein said monitoring step includes:

measuring the pressure of liquid in the system to obtain a first liquid pressure $P_1$, waiting a predetermined time interval, measuring the pressure of liquid in the system to obtain a second liquid pressure $P_2$, comparing the pressure $P_1$ to the pressure $P_2$, and providing a signal indicating leakage in the system when the difference between $P_1$ and $P_2$ exceeds a predetermined value.

7. The method of operating a pumping system in accordance with claim 6, wherein each of said steps of measuring the pressure of liquid in the system includes obtaining an average pressure of said system over a predetermined time interval.

8. A method of testing a pump cassette of a pumping system including a pump driver having a reciprocable pump piston, said pump cassette having pump means including a diaphragm positionable in operative association with the pump piston, the method comprising the steps of:

operating said pump driver to close liquid inlets and outlets of said pump cassette;

advancing said pump piston to displace said diaphragm to a first position to pressurize liquid in the cassette;

maintaining said pump diaphragm in said first position for a predetermined time interval;

retracting said pump piston so that said diaphragm moves to a second piston where said diaphragm is displaced less than in said first position;

measuring the pressure of liquid in the cassette of the system to obtain a first liquid pressure $P_1$;

waiting a predetermined time interval after measurement of $P_1$;

measuring the pressure of liquid in the cassette of the system to obtain a second liquid pressure $P_2$;

comparing the pressure $P_1$ to the pressure $P_2$ to ascertain any drop in pressure in the cassette of the system; and providing a signal indicating leakage in the cassette of the system when the difference between $P_1$ and $P_2$ exceeds a predetermined value.

9. The method of testing of claim 8, when each of said steps of measuring the pressure of liquid in the system includes obtaining an average pressure of said system over a predetermined time interval.

10. A method of operating a pump system, including positive displacement pump means having a deformable pump diaphragm which is displaced for creating positive liquid pressure in the system, the method comprising the steps of:

displacing said pump diaphragm to create a relatively high pressure in the system to stretch the pump diaphragm;

maintaining sufficiently high pressure in said system for a sufficient time interval to subject said stretched diaphragm to cold flow; and thereafter operating said pump means at a system pressure less than said relatively high pressure, with said displacing and maintaining steps acting to reduce the influence of cold flow of said diaphragm on subsequent operation of said pump means.

* * * * *